US00PP27113P2

(12) United States Plant Patent
Hansen

(10) Patent No.: US PP27,113 P2
(45) Date of Patent: Aug. 30, 2016

(54) ***×SEDORO* PLANT NAMED 'BLUE ELF'**

(50) Latin Name: ×*Sedoro*
Varietal Denomination: Blue Elf

(71) Applicant: Christopher M. Hansen, Holland, MI (US)

(72) Inventor: Christopher M. Hansen, Holland, MI (US)

( * ) Notice: Subject to any disclaimer, the term of this patent is extended or adjusted under 35 U.S.C. 154(b) by 66 days.

(21) Appl. No.: 14/121,759

(22) Filed: Oct. 14, 2014

(51) Int. Cl.
*A01H 5/12* (2006.01)

(52) U.S. Cl.
USPC ..... Plt./263.1

(58) Field of Classification Search
USPC ..... Plt./479, 263.1
See application file for complete search history.

(56) References Cited

PUBLICATIONS

USDA Plants Database Classification for Kingdom Plantae Down to Genus Sedum L., http://plants.usda.gov/java/ClassificationServlet?format=print&fileNamePF=classificationPF20160208103235343.txt&title=Sedum%20L., pulled from the internet on Feb. 8, 2016.*

* cited by examiner

*Primary Examiner* — Anne Grunberg
(74) *Attorney, Agent, or Firm* — Penny J. Aguirre

(57) ABSTRACT

A new cultivar of ×*Sedoro* plant named 'Blue Elf' characterized by its compact, non-flopping, mound-forming, low-growing groundcover plant habit, its compact and dense clusters of flowers that cover almost the entire plant surface (95%) in late summer, its numerous clusters of flowers that are hot pink in color in late summer, its foliage that is powder-blue in color during spring and early summer and becoming lightly suffused with rose-pink in mid-summer to fall, its heavy self-branching without pinching from early spring through mid-summer, its numerous lateral branches that elongate away from the central stem, and its inflorescences that have a strong sweet fragrance.

2 Drawing Sheets

Botanical classification: ×*Sedoro*.
Variety denomination: 'Blue Elf'.

BACKGROUND OF THE INVENTION

The present invention relates to a new and distinct cultivar of ×*Sedoro* plant. ×*Sedoro* is botanically an inter-generic hybrid between a *Sedum* of hybrid origin and ×*Orostachys malacophylla* var. *iwarenge*. The Inventor named the hybrid. ×*Sedoro* 'Blue Elf' is referred to hereinafter by its cultivar name, 'Blue Elf'. The new cultivar of ×*Sedoro* is a hardy herbaceous perennial grown for use as a landscape and container plant and is particularly suitable as a groundcover.

'Blue Elf' arose from an ongoing breeding program by the Inventor in Hudsonville, Mich., USA. The objective of the breeding program is to generate new inter-generic hybrids between *Orostachys* and *Sedum*; combining the blue foliage and compact habit of *Orostachys* with the hot pink flowers of *Sedum*.

The new cultivar arose from a controlled cross made in September of 2009 between an unnamed and unpatented plant of *Orostachys malacophylla* var. *iwarenge* from the Inventor's breeding program as the female parent and an unnamed and unpatented *Sedum* plant of hybrid origin from the Inventor's breeding program as the male parent. The Inventor selected 'Blue Elf' as a single unique plant in August of 2013 from the resulting seedlings.

Asexual reproduction of the new cultivar was first accomplished by stem tip cuttings in August of 2013 in Hudsonville, Mich. Propagation by stem tip cuttings has determined the characteristics to be stable and reproduced true to type in successive generations.

SUMMARY OF THE INVENTION

The following traits have been repeatedly observed and are determined to be the characteristics of the new cultivar. These attributes in combination distinguish 'Blue Elf' as a unique cultivar of ×*Sedoro*.

1. 'Blue Elf' exhibits a compact, non-flopping, mound-forming, low-growing groundcover plant habit.
2. 'Blue Elf' exhibits compact, dense clusters of flowers that cover almost the entire plant surface (95%) in late summer.
3. 'Blue Elf' exhibits numerous clusters of flowers that are hot pink in color in late summer.
4. "Blue Elf' exhibits foliage that is powder-blue in color during spring and early summer, becoming lightly suffused with rose-pink in mid-summer to fall.
5. 'Blue Elf' exhibits heavy self-branching without pinching (unique for a groundcover type *Sedum*) from early spring through mid-summer.
6. 'Blue Elf' exhibits numerous lateral branches that elongate away from the central stem.
7. 'Blue Elf' exhibits inflorescences that have a strong sweet fragrance and very attractive to bees.

The female parent differs from 'Blue Elf' in having long spikes of flowers that are white in color, in having lateral branches that are longer, in having leaves that are persistently blue-green in color (lack pink tinge), in being smaller in size, and in having a later blooming season. The male parent differs from 'Blue Elf' in being larger in size, in lacking lateral branches, in having a large, spreading mound plant habit, and in having leaves that are larger in size. 'Blue Elf' can be most closely compared to the *Sedum pluricaule* cultivar 'Rose Carpet' (not patented) and the *Sedum* cultivar 'Pure Joy' (U.S. Plant Pat. No. 24,194). 'Rose Carpet' is similar to 'Blue Elf' in having flowers that are pink in color and in having a low growing ground-cover plant habit. 'Rose Carpet' differs from 'Blue Elf' in having leaves that are smaller in size, in having inflorescences that are smaller in size, in being smaller in overall size, in lacking the production of lateral branches, and in having less dense coverage of flowers during peak bloom (60%). 'Pure Joy' is similar to 'Blue Elf' in having flowers that are pink in color, in having a compact plant habit, and in having flowers that cover 95% of the surface of the plant during peak bloom. 'Pure Joy' differs from 'Blue Elf' in having leaves that emerge blue-green in color turning to solid green in color by mid-summer, in having leaves that are longer and thinner, in having leaves with serrated margins, in being larger in overall size, in lacking the production of numerous lateral branches.

BRIEF DESCRIPTION OF THE DRAWINGS

The accompanying colored photographs illustrate the overall appearance and distinct characteristics of the new ×*Sedoro*.

The photograph in FIG. 1 is of a plant about 6 months in age as grown outdoors in a 1-gallon container in Hudsonville, Mich. The photograph in FIG. 1 provides a view of the foliage of 'Blue Elf' as it takes on a slight pink coloration in early summer.

Figure 1:
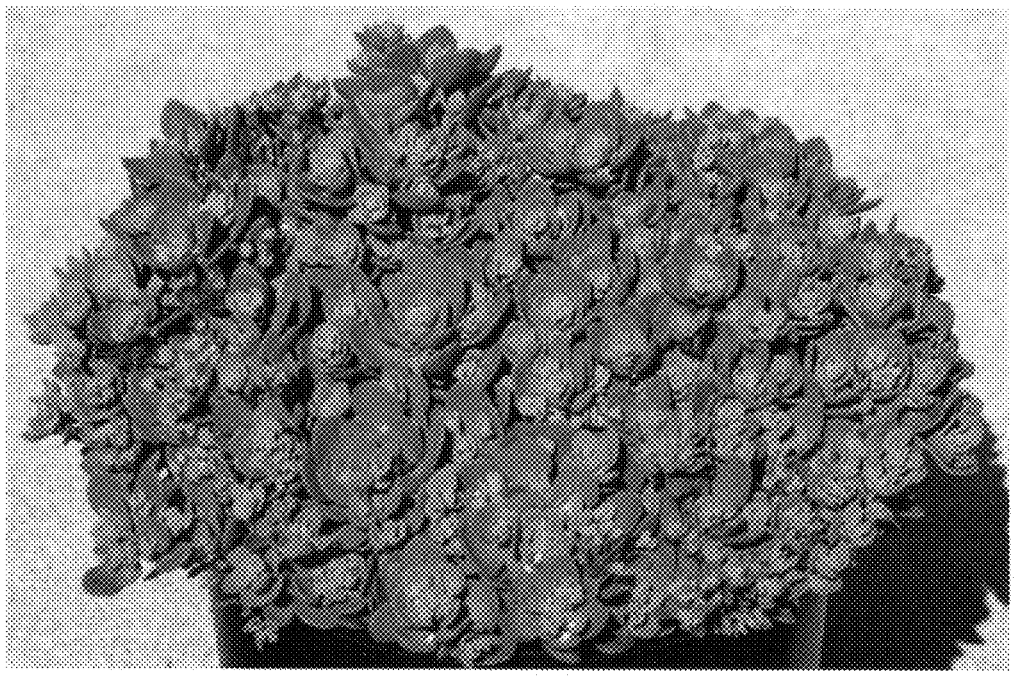
Figure 2:
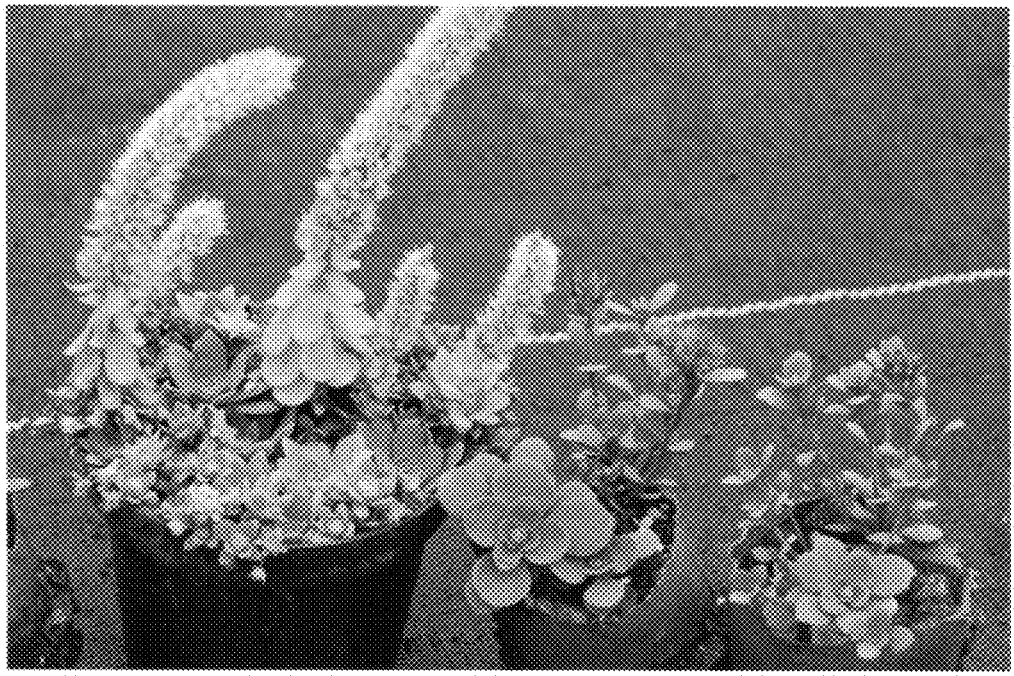

The photograph in FIG. 2 provides a comparison view of the inflorescences of the female parent on the left (3 months in age, 1 qt. container) and the inflorescences of 2 plants of 'Blue Elf' on the right (2 months in age, 3-inch plug).

Figure 3:
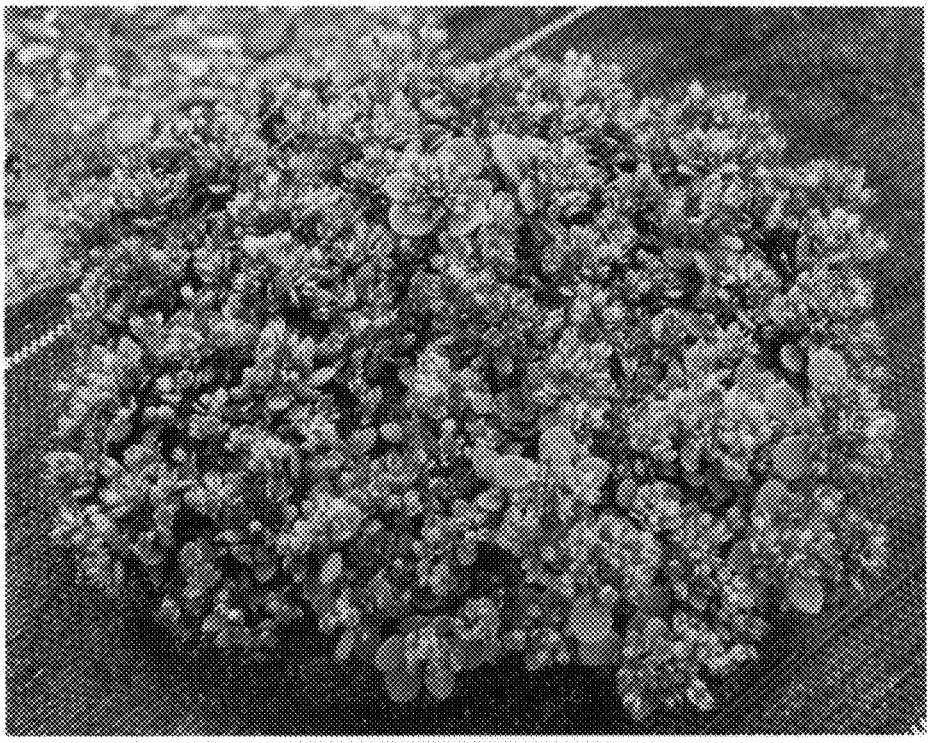

The photograph in FIG. 3 is of a plant about 2 years in age as grown outdoors in the ground in Hudsonville, Mich. The photograph in FIG. 3 provides a view of 'Blue Elf' in bloom.

Figure 4:
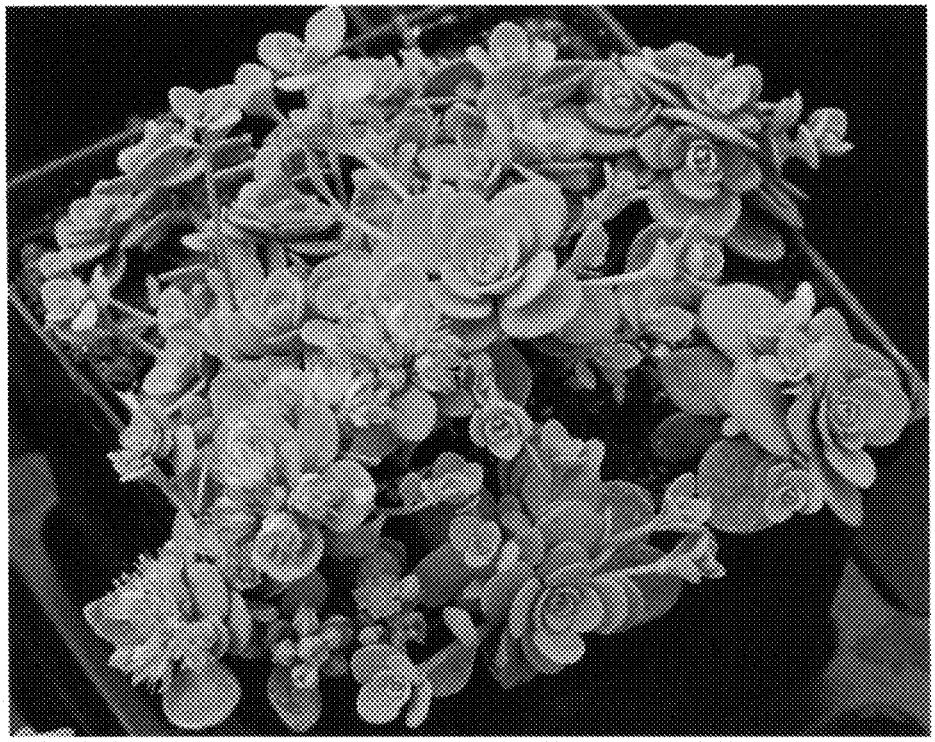

The photograph in FIG. 4 is of a plant 3 months in age as grown in a 1-quart container. The photograph in FIG. 4 shows the numerous lateral branches emerging and elongating from each plant stem.

The colors in the photographs may differ slightly from the color values cited in the detailed botanical description, which accurately describe the colors of the new ×*Sedoro*.

DETAILED BOTANICAL DESCRIPTION

The following is a detailed description of the new cultivar as observed on 3 month-old plants of 'Blue Elf' as grown in one-quart containers in Hudsonville, Mich. The phenotype of the new cultivar may vary with variations in environmental, climatic, and cultural conditions, as it has not been tested under all possible environmental conditions. The color determination is in accordance with The 2001 R.H.S. Colour Chart of The Royal Horticultural Society, London, England, except where general color terms of ordinary dictionary significance are used.

General description:

*Blooming period.*—From mid-August through mid-October in Michigan.

*Plant type.*—Herbaceous perennial.

*Plant habit.*—Compact, non-flopping, mound-forming, low-growing groundcover.

*Height and spread.*—Reaches about 7.6 cm in height and about 38 cm in spread.

*Hardiness.*—At least hardy in U.S.D.A. Zones 4 to 9.

*Diseases pest*—Highly resistant to *sedum* foliage blight caused by *Botrytis cinerea* with no occurrence of observed in a 6 year period.

*Root description.*—Fibrous.

*Propagation.*—Stem tip cuttings.

*Growth rate.*—Typical for a groundcover type *sedum*.

Stem description:

*Stem shape.*—Round.

*Stem size.*—An average of 12 cm in length (including terminal peduncle), and 3 mm in width with lateral branches an average of 7 cm in length and 2 mm in width.

*Internode length.*—Average of 2 cm.

*Stem color.*—Spring and mid-summer; 138B to 138C suffused with N79, mature bark; 199B.

*Stem surface.*—Glabrous.

*Branching habit.*—Well-branched with basal and lateral branching; about 10 to 12 lateral branches per basal branch.

Foliage description:

*Leaf shape.*—Rhombic to orbicular.

*Leaf division.*—Simple.

*Leaf arrangement.*—Whorled (sometimes opposite).

*Leaf base.*—Truncate.

*Leaf apex.*—Acute.

*Leaf venation.*—Not conspicuous, color matched leaf color.

*Leaf margins.*—Entire.

*Leaf attachment.*—Sessile.

*Leaf orientation.*—Nearly horizontal to slightly upward, slightly cupped.

*Leaf texture.*—Thick, succulent.

*Leaf surface.*—Glandular and glaucous.

*Leaf color.*—Spring upper and lower surface; a blend between 122A and N138C, mid-summer and fall upper surface; a blend of N138B and N189B suffused with 64B at the margin and lower surface; a blend of N138B and N189B suffused with 64B.

*Leaf size.*—Average of 2.8 cm in length and 1.3 cm in width.

Flower description:

*Inflorescence type.*—Dense, slightly rounded cymes with an average of 9 terminal forked branches at terminus and upper lateral nodes.

*Inflorescence size.*—An average of 2.5 cm in diameter and 2 cm in depth (inclusive of all branches per stem).

*Lastingness of inflorescence.*—About two months.

*Flower type.*—Perfect, spreading, 5-starred.

*Flower number.*—Average of 25 flowers per branched cyme, 100 flowers per stem.

*Flower fragrance.*—Strong sweet fragrance (detected up to 3 m away) and very attractive to bees.

*Flower buds.*—Ovate in shape, about 6 mm length and 4 mm in width, ribbed surface, color; a blend of 138A, N74C to N74D and N79B.

*Flower size.*—About 5 mm in depth and 9 mm in diameter.

*Peduncles.*—Oval in shape, an average of 1.5 cm in length and 1.2 mm in width, a blend of 138B suffused with 187B in color, glabrous surface, peduncle leaves; an average of 2 per individual cyme, oblanceolate in shape, an average of 5 mm length and 2 mm in width, a blend of 138B suffused with 187B, glandular and glaucous on both surfaces.

*Pedicels.*—Round in shape, an average of 6 cm in length and 1 mm in width, 138B suffused with 187B in color, glabrous surface.

*Calyx.*—5-parted fused to tubular base, tips held nearly upright, about 4 mm in length and 3 mm in width.

*Sepals.*—5, tube; about 2.5 mm in length and 1 mm in width, tips; about 2 mm in length and 0.7 cm in width, lanceolate in shape, color; 138B suffused with 187B on both surfaces, entire margin, narrowly acute apex, fused base, glaucous on both surfaces.

*Petals.*—5, spreading, 6 mm in length and 2.5 mm in width, elliptic in shape, truncate base, acute apex, entire margin, color of inner and outer surfaces when opening; N74A to N74D with 13C at the center, color when mature; inner surfaces; 75A to 75D suffused with a blend of 75D and N155B especially at the base, outer surfaces; 75A to 75B with center 13D and spotted 71A and base 75D, becoming dry and upright and a blend of 13B to 13C and 165A to 165B towards the base, translucent, glabrous on both surfaces.

Reproductive organs:

*Pistils.*—5, showy, held erect, about 6 mm in length 1.5 mm in width, stigma; 0.5 mm in width and 75A in color, style; 5.5 mm in length, 1.5 mm in width, lanceolate in shape and N155C suffused with 75A in color, ovary; small, single celled and translucent in color.

*Stamens.*—10, about 5 mm in length, filament; very fine and 75B to 75D in color, anther; basifixed, about 4 mm in length and 0.5 mm in width, a blend of 202A in color, pollen is moderate in quantity and about 158C in color.

*Fruit.*—Fruit and seed production has not been observed.

It is claimed:

1. A new and distinct variety of ×*Sedoro* plant named 'Blue Elf' as described and illustrated herein.

* * * * *